United States Patent
Hashimoto et al.

(10) Patent No.: US 10,557,165 B2
(45) Date of Patent: *Feb. 11, 2020

(54) NUCLEIC ACID DETECTION METHOD AND ASSAY KIT

(71) Applicant: Kabushiki Kaisha Toshiba, Minato-ku (JP)

(72) Inventors: Koji Hashimoto, Atsugi (JP); Keiko Ito, Kawasaki (JP); Mika Inada, Tokyo (JP)

(73) Assignee: KABUSHIKI KAISHA TOSHIBA, Minato-ku (JP)

( * ) Notice: Subject to any disclaimer, the term of this patent is extended or adjusted under 35 U.S.C. 154(b) by 119 days.

This patent is subject to a terminal disclaimer.

(21) Appl. No.: 15/691,337

(22) Filed: Aug. 30, 2017

(65) Prior Publication Data

US 2018/0127814 A1 May 10, 2018

(30) Foreign Application Priority Data

Nov. 4, 2016 (JP) .................. 2016-216159

(51) Int. Cl.
*C12Q 1/68* (2018.01)
*C12Q 1/6837* (2018.01)
(Continued)

(52) U.S. Cl.
CPC ......... *C12Q 1/6837* (2013.01); *C12Q 1/6823* (2013.01); *C12Q 1/6825* (2013.01);
(Continued)

(58) Field of Classification Search
None
See application file for complete search history.

(56) References Cited

U.S. PATENT DOCUMENTS 8,765,373 B2 * 7/2014 Majda ............... C12Q 1/6825
435/283.1
2003/0129632 A1 * 7/2003 Mori .................. C12Q 1/6844
435/6.11
(Continued)

FOREIGN PATENT DOCUMENTS

JP 2008-525780 7/2008
JP 4505414 7/2010
(Continued)

OTHER PUBLICATIONS

Tomita et al, Nature Protocols, vol. 3, pp. 877-882 and Corrigendum, published online Apr. 24, 2008; corrected online Jan. 12, 2012.*
(Continued)

*Primary Examiner* — Robert T. Crow
(74) *Attorney, Agent, or Firm* — Oblon, McClelland, Maier & Neustadt, L.L.P.

(57) ABSTRACT

According to one embodiment, a method for detecting target nucleic acid includes the following steps. (A) A reaction field is formed by placing a reaction mixture on an electrode, and the reaction mixture contains the sample, a primer set, an amplification enzyme, 4 mM to 30 mM of magnesium ion, and a redox probe. The redox probe has an oxidation reduction potential, which generates an electric signal of which amplitude increases. (B) The reaction field is maintained under an amplification reaction condition. (C) The electric signal is detected with the electrode. (D) Existence or quantity of the target nucleic acid is determined.

12 Claims, 9 Drawing Sheets

Specification includes a Sequence Listing.

(51) Int. Cl.
*C12Q 1/6823* (2018.01)
*C12Q 1/6825* (2018.01)
*C12Q 1/6851* (2018.01)
*C12N 15/09* (2006.01)

(52) U.S. Cl.
CPC ............ *C12Q 1/6851* (2013.01); *C12N 15/09* (2013.01); *C12Q 2525/301* (2013.01); *C12Q 2527/101* (2013.01); *C12Q 2537/1373* (2013.01); *C12Q 2537/163* (2013.01); *C12Q 2563/113* (2013.01)

(56) References Cited

U.S. PATENT DOCUMENTS

| | | | |
|---|---|---|---|
| 2004/0023258 A1* | 2/2004 | Patolsky | C12Q 1/6816 |
| | | | 435/6.11 |
| 2004/0086892 A1 | 5/2004 | Crothers et al. | |
| 2004/0086894 A1 | 5/2004 | Crothers et al. | |
| 2004/0086895 A1 | 5/2004 | Crothers et al. | |
| 2007/0298415 A1* | 12/2007 | Uemori | C12Q 1/6844 |
| | | | 435/6.12 |
| 2008/0135419 A1 | 6/2008 | Roblin et al. | |
| 2014/0220667 A1 | 8/2014 | Safavieh et al. | |
| 2015/0219593 A1 | 8/2015 | Kawai et al. | |
| 2016/0177387 A1* | 6/2016 | Roy | C12Q 1/6876 |
| | | | 435/6.1 |
| 2017/0191122 A1 | 7/2017 | Hashimoto et al. | |
| 2018/0363043 A1 | 12/2018 | Hashimoto et al. | |

FOREIGN PATENT DOCUMENTS

| | | |
|---|---|---|
| JP | 6346242 B2 | 6/2018 |
| JP | 2019-53 | 1/2019 |
| WO | WO2014/027580 A1 | 2/2014 |
| WO | WO 2016/136033 A1 | 9/2016 |

OTHER PUBLICATIONS

Patolsky et al, Angew, Chemie Int. Ed., vol. 41, pp. 3398-3402, 2002.*

Minhaz Uddin Ahmed, et al. "Real-time electrochemical detection of pathogen DNA using electrostatic interaction of a redox probe", Analyst, vol. 138, No. 3, 2012, pp. 907-915.

Bo Yao, et al. "Sensitive detection of microRNA by chronocoulometry and rolling circle amplification on a gold electrode", Chemical Communications, vol. 50, No. 68, 2014, pp. 9704-9706.

* cited by examiner

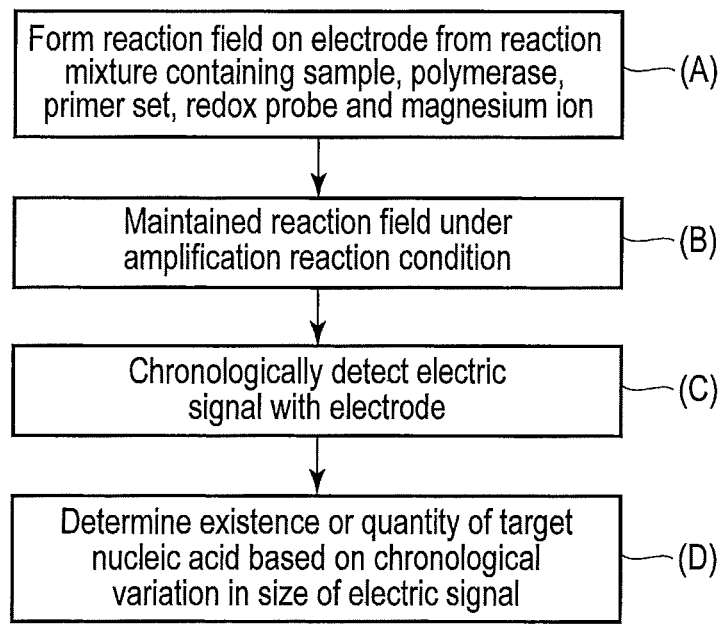
F I G. 1
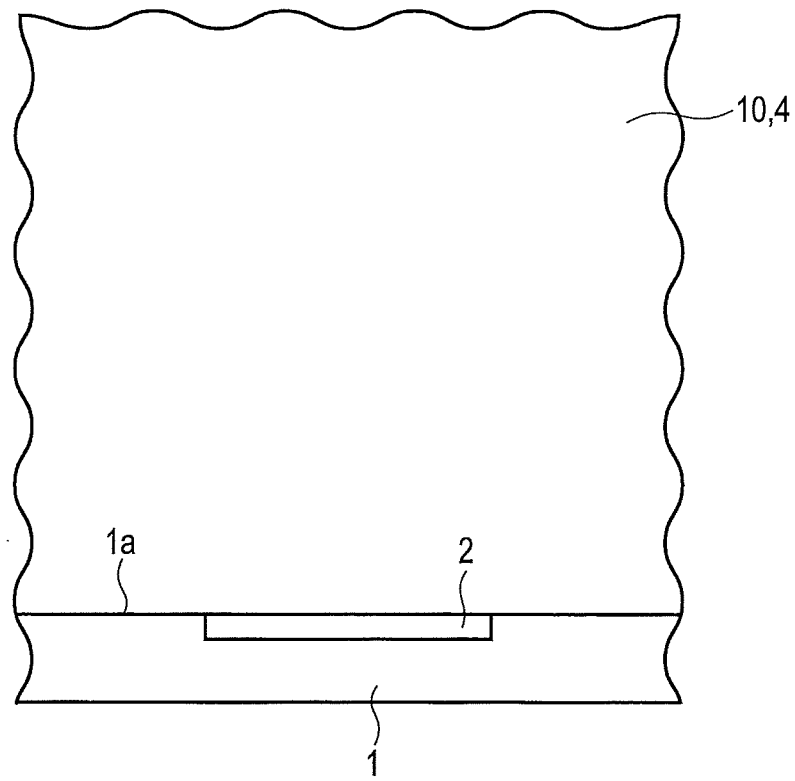
F I G. 2

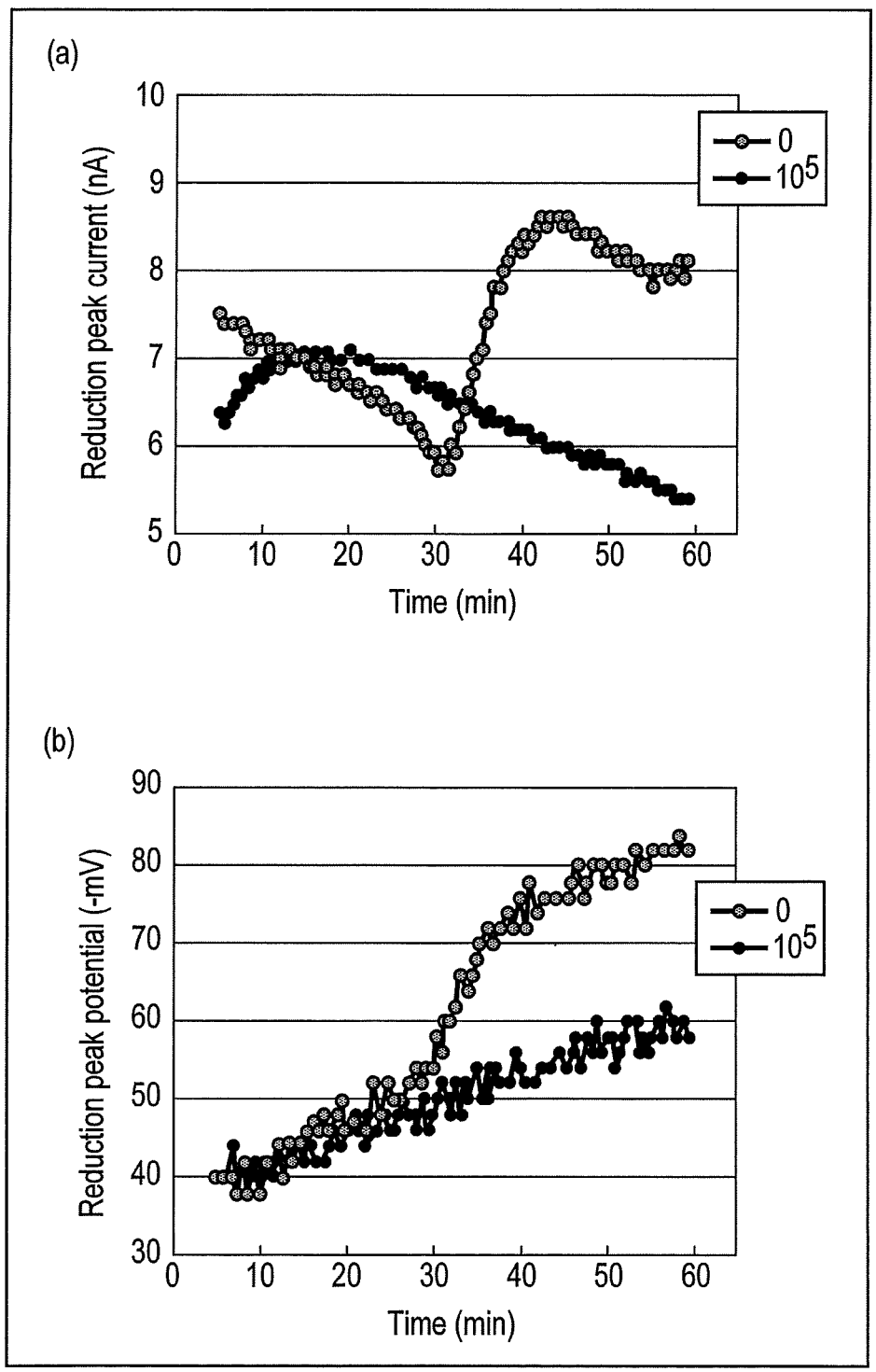
F I G. 6

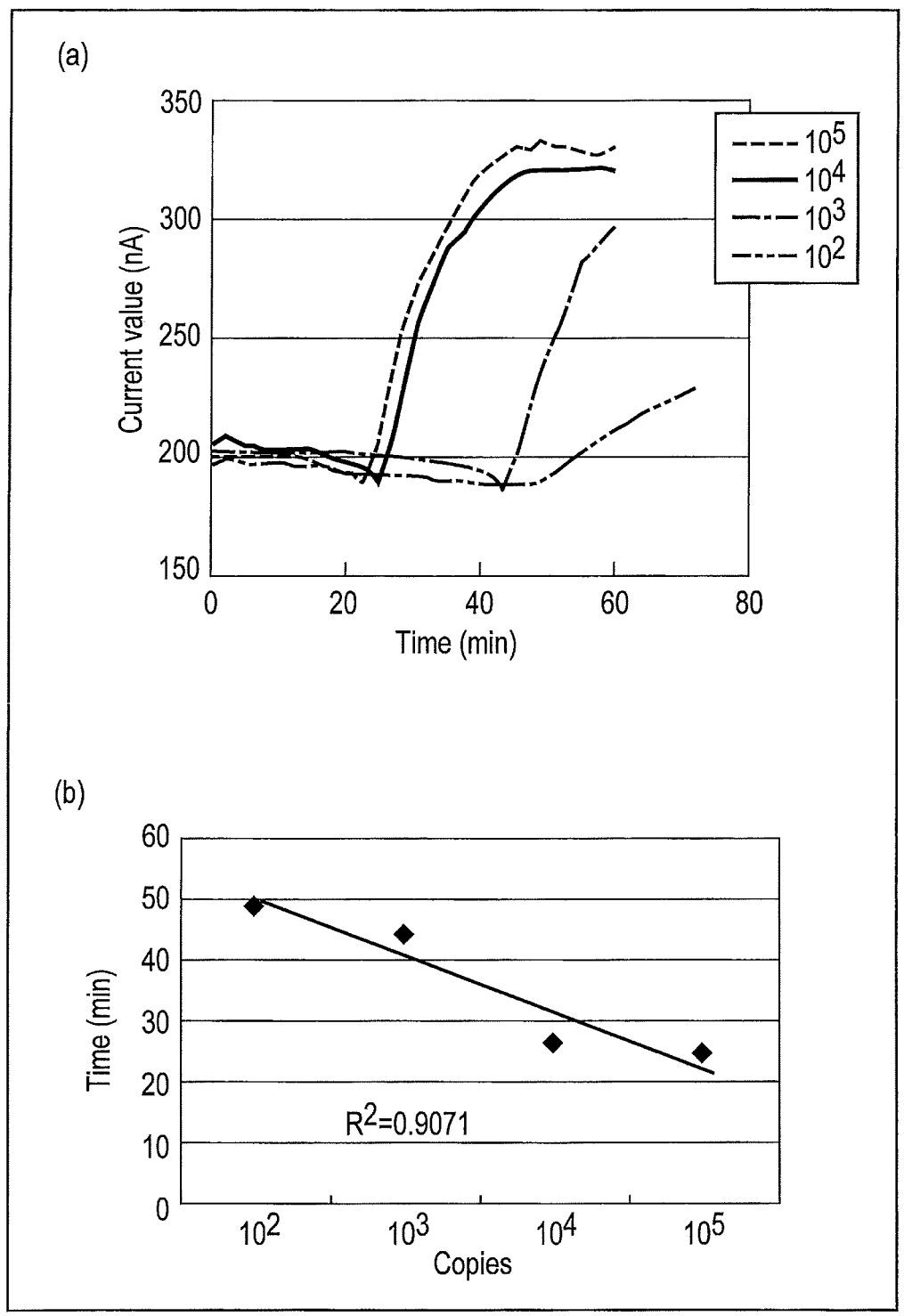
F I G. 11

NUCLEIC ACID DETECTION METHOD AND ASSAY KIT

CROSS-REFERENCE TO RELATED APPLICATIONS

This application is based upon and claims the benefit of priority from Japanese Patent Application No. 2016-216159, filed Nov. 4, 2016, the entire contents of which are incorporated herein by reference.

FIELD

Embodiments described herein relate generally to a nucleic acid detection method and an assay kit.

BACKGROUND

At present, with progress of genetic-testing technology, the nucleic acid testing is carried out in various scenes, such as clinical diagnosis and criminal investigations. The target genes are detected or quantified by methods such as the real-time PCR method or microarray method. For example, the real-time PCR method is accompanied by the amplification of nucleic acid, and therefore its sensitivity is high and the quantitative range is wide. On the other hand, with the microarray method, it is possible to detect tens of thousands or more kinds of target genes simultaneously. Further, a detection method which combines these methods has been proposed.

Under such circumstances, there is a demand for further development of a detection method which can detect nucleic acid simply at high sensitivity.

BRIEF DESCRIPTION OF THE DRAWINGS

FIG. 1 is a flowchart showing an example of a nucleic acid detection method in an embodiment.

FIG. 2 is a diagram showing an example of a substrate of the embodiment.

FIG. 6 is a diagram showing the experimental results in Example 1.

FIG. 11 is a diagram showing the experimental results in Example 4.

DETAILED DESCRIPTION

Figure 3:
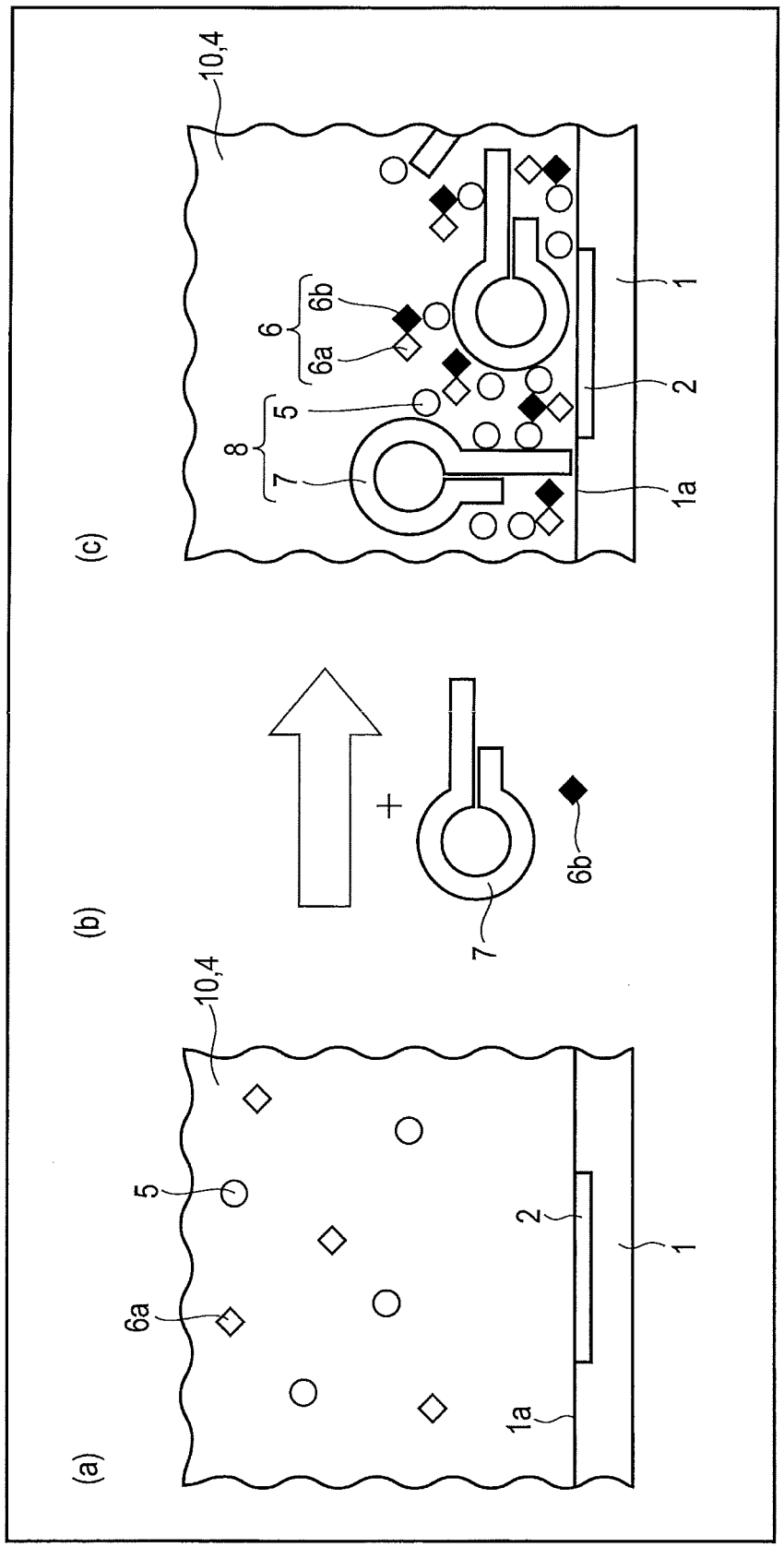
FIG. 3 is a diagram illustrating a mechanism of the detection, speculated in the embodiment.

Various embodiments will be described below with reference to the accompanying drawings. Further, the drawings are schematic diagrams designed to assist the reader to understand the embodiments easily. Thus, there may be sections where the shape, dimensions, ratio, etc., are different from those of the actual devices, but they can be re-designed as needed with reference to the following explanations and publicly known techniques.

In general, according to one embodiment, the nucleic acid detection method is a method for detect a target nucleic acid in a sample. The target nucleic acid includes the first sequence. FIG. 1 shows a brief flow of the nucleic acid detection method according to the embodiment.

The nucleic acid detection method comprises steps (A) to (D) set forth below. (A) A reaction field is formed by placing a reaction mixture on an electrode, and the reaction mixture contains the sample, a primer set, a corresponding amplification enzyme, 4 mM to 30 mM in concentration of magnesium ion, and a redox probe. The primer set for amplifying the first sequence to obtain an amplification product, wherein the primer set contains at least a first primer complementary to a terminal of the first sequence and a second primer homologous to the other terminal of the first sequence. The redox probe has an oxidation reduction potential of −0.5 V to 0.5 V, which generates a detectable electric signal of which amplitude increases with an increase in an amount of the amplification product existing in the reaction field. (B) The reaction field is maintained under an amplification reaction condition. (C) The electric signal from the redox probe is chronologically detected with the electrode while maintaining the reaction field under the amplification reaction condition. (D) Existence or quantity of the target nucleic acid is determined based on chronological variation in the amplitude of the electric signal, obtained in (C).

In step (A), a reaction mixture is placed on an electrode, thus forming a reaction field. A "reaction field" is a region where an amplification reaction is carried out. The region is defined by the reaction mixture. In other words, a reaction field may be a region where a reaction mixture exists.

The reaction mixture contains a sample, a primer-set, an amplification enzyme which corresponds thereto, a specific concentration of magnesium ion and a redox probe.

The sample is a substance to be examined as to the presence/absence or quantity of a target nucleic acid. In other words, the sample may be an object to be analyzed, which may include a target nucleic acid. The sample may be, for example, in a liquid form. For example, the sample may be bio-materials including blood, serum, leukocyte, urine, feces, sweat, saliva, oral mucosa, expectoration, lymph, spinal fluid, lacrimal fluid, mother milk, amniotic fluid, semen, tissue, biopsy and culture cells, environmental materials collected from the environment, artificial nucleic acids or the like, or mixtures of those. Further, a preparation formulated using any of above materials may as well be used as the sample. For example, a pretreatment may be carried out on any of above materials to be used as a sample in the embodiment. The pretreatment may be any conventional means known by itself, such as a fragment, homogenization or extraction, for example. For example, any of above materials may be collected from an organism or environment, and formulated into a condition suitable for the nucleic acid detection. For example, a liquid containing a nucleic acid component which is obtained by extracting a nucleic acid from any of above materials by any means can be used as the sample.

The target nucleic acid is a nucleic acid to be detected. The target nucleic acid includes a first sequence. The first sequence is a sequence which can be an index of the target nucleic acid, and may be selected from a full length of the sequence of the target nucleic acid. For example, the first sequence may be a sequence specific to the target nucleic acid. The target nucleic acid is a single strand nucleic acid. The state of the target nucleic acid in the sample may be single-stranded. Or, the state of the target nucleic acid in the sample may be a double strand formed from a target nucleic acid and a nucleic acid chain complementary to the target nucleic acid. For example, the sample to be examined may contain both a single-stranded target nucleic acid and a double-stranded target nucleic acid. The length of the target sequence may be, for example, 50 to 500 bases, and preferably, 100 to 300 bases.

The length of the first sequence may be, for example, 3 to 10 bases, 10 to 20 bases, 20 to 30 bases, 30 to 40 bases, 40 to 50 bases, 50 to 60 bases, 60 to 70 bases, 70 to 80 bases, 80 to 90 bases or 90 to 100 bases, and preferably, 10 to 50 bases.

The amplification or amplification reaction means a process in which a target nucleic acid, or a complementary nucleic acid thereof, or an amplification product of each of these is continuously replicated using those as a template to produce an amplification product.

The amplification method may be, for example, PCR, LAMP, RT-LAMP, SDA, NASBA, RCA, LCR, TMA, SmartAmp (registered trademark) or ICAN (registered trademark). Further, a reverse transcription reaction may be carried out together with the amplification reaction as needed, for example, simultaneously.

The primer set is designed and/or selected to amplify the first sequence as the index using the target nucleic acid as a template so that an amplification product comprising the first sequence can be obtain, and the target nucleic acid can be detected. The primer set contains a first primer complementary to one terminal of the first sequence and a second primer homologous to the other terminal of the first sequence. With these primers, a range to be amplified on the target nucleic acid is specified.

For example, when the target nucleic acid in a sample is a single-stranded DNA, a complementary strand is formed by a primer set, and further the amplification reaction advances using it as a template. Moreover, when the target nucleic acid is RNA, a reverse transcription reaction is carried out and the reverse transcription product is subjected to the amplification reaction.

For example, in the case of a primer set for PCR, one primer set may contain one kind of forward primer as the first primer and one kind of reverse primer as the second primer.

Moreover, for example, in the case of a primer set for LAMP, one primer set may contain an FIP primer as the first primer and a BIP primer as the second primer. The primer set for LAMP may further contain an F3 primer, B3 primer and LP gas primer, that is, LF primers and/or LB primers. The LAPM amplification product has a stem loop structure which includes a loop part which is a single-stranded region, and a stem part which is double-stranded region.

The corresponding amplification enzyme is an amplification enzyme used for an amplification reaction. The amplification enzyme may be selected based on the kind of target nucleic acid, the amplification method, the primer set, and the presence/absence of a reverse transcription reaction, etc. The amplification enzyme may be DNA polymerase, RNA polymerase, or the like for example.

The DNA-polymerase may be Bst, Bst2.0, Bst3.0, GspSSD, GspM, Tin, Bsm, Csa, 96-7, phi29, Omini-Amp (registered trademark), Aac, Bca BEST (registered trademark), Displace Ace (registered trademark), SD, Strand Displace (registered trademark), TOPOTAQ, Isotherm2G, Taq or a combination of any of these, for example. The kind of polymerase may be selected as needed. But Bst, GspSSD, or Tin is preferable since the sensitivity of detection can be increased therewith. The reaction liquid may further contain any type of reverse transcriptase in addition to amplification enzyme.

Magnesium ion may be contained in the reaction mixture at a concentration of 4 mM to 30 mM to the reaction mixture.

The inventors of the embodiments have found that in a reaction mixture containing the above-specified concentration of magnesium, the amplitude of the electric signal detected with the electrode increases with the increase in the amount of the amplification product present in a reaction field.

Conversely, Ahmed et al. (Analyst 138, 907-15 (2013)) report a detection carried out based on the decrease in the electric signal, caused by the increase in the amplification product, as an index. Note, however, that the decrease in an electric signal may occur not only by change in the amount of an amplification product present, but also by mixing of a reaction inhibiting material or the like. On the other hand, the increase in the electric signal, used as the index in this embodiment, is not easily affected by a reaction inhibiting material or the like. Rather, the change in the amount of an amplification product is substantially directly reflected. Thus, higher-precision detection is achievable.

In the reaction mixture with a concentration of magnesium ion being 4 mM or higher, the amplification reaction is promoted. Further, with the generation of the amplification product, magnesium pyrophosphate, in which pyrophosphoric acid and magnesium ion are bonded together, is fully generated. As a result, magnesium pyrophosphate precipitates in the reaction mixture. Although a detailed explanation will be provided later, due to the generation of the precipitate, the amount of the amplification product present in the reaction field is reflected as an increase in the amplitude of the electric signal from the redox probe.

The concentration of magnesium ion contained in the reaction mixture should more preferably 4 to 12 mM, in which case magnesium pyrophosphate more easily precipitates. Even more preferable magnesium ion concentration is 5 to 10 mM.

Magnesium ion can be contained in a reaction mixture by adding, for example, magnesium sulfide or magnesium chloride in the reaction mixture.

With a concentration of magnesium ion of 4 mM to 30 mM in the reaction mixture, the amplification reaction is promoted, thereby making it possible to amplify various types of sequences of a wide range efficiently, for example, without depending on the sequence. Thus, various types of sequences can be detected efficiently, for example.

A redox probe is a substance which has an oxidation reduction potential of $-0.5$ V to $0.5$ V and generates a detectable electric signal. The detectable electric signal may be, for example, an oxidation reduction potential or oxidation reduction current of the redox probe. An electric signal from the redox probe is detected with an electrode in contact with the reaction mixture. Further, the redox probe is electrostatically coupled with the amplification product in the reaction mixture.

The redox probe may be a complex, for example. The complex may contain, for example, ruthenium (Ru), rhodium (Rh), platinum (Pt), cobalt (Co), chromium (Cr), cadmium (Cd), nickel (Ni), zinc (Zn), copper (Cu), osmium (Os), iron (Fe), or silver (Ag) as a central metal. The complex concerned may be, for example, amine complex, cyano complex, halogen complex, hydroxy complex, cyclopentadienyl complex, phenanthroline complex or bipyridine complex.

The redox probe may be a pigment, for example. The pigment may be, for example, methylene blue, Nile blue or crystal violet.

The redox probe is, for example, ruthenium hexaamine (RuHex). In this case, with application of voltage to the electrode, $RuHex^{3+}$ is reduced to $RuHex^{2+}$ and electrons are released. As these electrons flow into the electrode, the oxidation reduction potential or current of RuHex is detected with the electrode. The redox probe should preferably be RuHex, since in which case the oxidation reduction potential is high and the sensitivity of the detection is enhanced.

The concentration of the redox probe in the reaction mixture may be 0.1 µM to 100 mM, for example, preferably, 25 µM to 3 mM, and even more preferably 1 mM, in which case the sensitivity of the nucleic acid detection is enhanced. In particular, when the redox probe is RuHex, it is desirable that the redox probe be contained in a range of 25 µM to 3 mM. If the amount of the redox probe in the reaction mixture is excessively low, the binding to the amplification product may be insufficient, which may cause the deterioration of the detection sensitivity. On the other hand, when it is excessive, the amplification reaction may be inhibited.

The reaction mixture may contain an ingredient required for the amplification reaction in addition to the above-listed ingredients. Such an additional ingredient may be, for example, salt, a substrate such as deoxynucleoside triphosphate (dNTP) required to form a new polynucleotide chain starting from a primer as the starting point, a thickener as a reaction reagent, a buffer for pH control, a surfactant, ion that increases the annealing specificity, ion used as a cofactor for the amplification enzyme and/or, when reverse transcription is carried out simultaneously, reverse transcriptase and a substrate required therefor.

The salt may be any conventionally known salt used to, for example, maintain suitable amplification environment in a nucleic acid amplification reaction. To maintain a suitable amplification environment in a nucleic acid amplification reaction may mean that, for example, the amplification enzyme maintains the tertiary structure so as to optimize the nucleic acid amplification activity. The salt may be potassium chloride, for example. The concentration of salt in the reaction mixture should desirably be, for example, 5 mol/L to 300 mol/L.

The electrode is configured to detect electric signals. More specifically, a reaction field is formed on the electrode, and the surface of at least a part of the electrode is in contact with the reaction mixture. With this structure, an electric signal from the redox probe contained therein is detected. The electrode should preferably comprise a flat plane on a part of the surface thereof. When a reaction field is formed on this flat plane, the reaction field may be placed, for example, so as to cover the entire flat plane of the electrode, or to include the flat plane, or may be placed in a region partitioned by the flat plane.

For example, the electrode may be arranged inside the reaction container, for example, so as to be in contact with the bottom thereof or to be buried in the bottom, or may be disposed on a tabular substrate.

FIG. 2 shows an example of the relationship between the reaction mixture and the electrode in the nucleic acid detection method according to the embodiment.

The reaction field may be supported with a substrate, for example, which exposes the surface of the electrode from the surface of the substrate to be flush therewith. In that case, the reaction field may be formed on the electrode disposed on an upper surface of the substrate. The substrate 1 is in a solid phase. The substrate 1 may be, for example, resin, glass or silicon. The electrode 2 is disposed on the upper surface 1a of the substrate 1. The electrode 2 may be a metal film formed on the surface of the substrate 1. The metal film may be, for example, gold. The metal film should desirably be gold because of its high sensitivity. The substrate 1 may comprise a reference pole and a counter pole in addition to the electrode 2.

With the reaction mixture 4 brought on the electrode 2 described above, the reaction field 10 may be formed from the reaction mixture 4 present on the electrode 2.

The ingredients to be contained in the reaction mixture described above should just be present in the reaction mixture at the time when it forms the reaction field. Therefore, these ingredients may be added to the reaction mixture, for example, before the reaction mixture is brought to the region which gives rise to the reaction field. Alternatively, some of the ingredients of the reaction mixture may be prepared separately, and thus some may be brought to the reaction mixture at the same time as that when the reaction mixture is brought to the region to become the reaction field, or before or after that time. Or before the reaction mixture is brought to the region to become the reaction field, some of the ingredients may be releasably immobilized to a solid phase or the like which is in contact with the reaction field, and brought into the reaction mixture by being released when the reaction mixture is brought thereto.

For example, when a primer set is releasably immobilized in advance, the primer set may be immobilized in, for example, a primer-immobilized region (not shown) which exists in the solid phase which is in contact with the reaction field 10 of the substrate 1.

In a further embodiment, the overall shape of the substrate 1 may be, for example, a container-like, a tabular, a globular, a rod-like, or a part of any of these. The size and form of the substrate 1 may be selected arbitrarily by the operator. Further, a substrate including a flow channel may be used as the substrate 1.

In a further embodiment, the substrate may comprise a plurality of electrodes arranged in an array as will be explained later.

In a process (B), the reaction field formed in the process (A) is maintained under an amplification reaction condition.

The amplification reaction condition may be selected based on the amplification method selected, the type of the primer set, the kind of the target nucleic acid, the kind of the amplification enzyme, and/or the like. For example, the amplification reaction condition may be an isothermal or temperature-varying amplification reaction condition. Here, the isothermal amplification reaction condition is desirable. The isothermal amplification reaction condition should desirably be a LAMP amplification reaction condition. When adopting the isothermal amplification reaction condition, the reaction temperature may be selected depending on the kind of the amplification enzyme used for the nucleic acid detection method. The temperature may be, for example, 25° C. to 70° C., and preferably, 55° C. to 65° C. By maintaining the reaction field under the reaction condition, the amplification reaction is carried out and the amplification product can be produced.

In a process (C), while maintaining the field under the amplification reaction condition, electric signals from the redox probe are detected chronologically with the electrode.

The electric signals can be detected by obtaining, for example, a current value, a potential value, a capacitance value or an impedance value with the electrode. The electric signals may be detected by measuring, for example, values of a plurality of kinds of electric signals such as a current value and a potential value. The detection may be performed by, for example, a device which can detect a current value, a potential value, a capacitance value or an impedance value. Such a device may be any of the well-known devices.

The electric signals may be detected chronologically, which may be continuous or intermittently, that it, at a plurality of time points at a predetermined time interval. For example, the continuous detection of an electric signal may be monitoring of the electric signal. When an amplification product nucleic acid exists, a higher value of the electric signal is obtained as compared to the case where no amplification product nucleic acid exists by detecting from the start of the amplification reaction chronologically for a desired time. Or the rise of electric signal is observed at an earlier time. Or, before the electric signal increases with the increase in the amplification product, such a phenomenon is also observed that the peak of the oxidation reduction potential once shifts in a negative direction. Based on this, even a higher-precision measurement may be carried out by combining the shift of the peak potential in the negative direction, the amount of the electric signal and the peak shift measurement of the oxidation reduction potential.

In a process (D), the existence and/or quantity of a target nucleic acid are determined based on the chronologically change in the amplitude of the electric signal obtained in the process (C) above.

The existence and/or the quantity of the target nucleic acid may be determined based on the result obtained by measuring the time required for the detection signal to exceed a predetermined threshold as a rise time. Alternatively, the existence and/or the quantity of the target nucleic acid may be determined by calculating the amount of the target nucleic acid in a sample with a method comprising the following processing steps: preparing several different standard sample nucleic acids whose amounts of nucleic acids existing are already known; measuring using the standard sample nucleic acids and preparing a calibration curve from the measurement result obtained for the amount of each nucleic acid; and comparing the measurement result of the target nucleic acid with the calibration curve prepared.

According to the nucleic acid detection method of the embodiment, it is possible to detect and quantify a target nucleic acid in more simple way and at higher sensitivity than those of the conventional techniques. Moreover, according to the nucleic acid detection method of the embodiment, even many more kinds of target nucleic acids are detectable than with the conventional techniques.

With the embodiment described above, the amount of an amplification product existing can be reflected as an increase in electric signal in a simple way. As a result, it becomes possible to detect or quantify a target nucleic acid in a sample with high precision in a simple way.

One reason why the amount of an amplification product existing can be detected as an increase in electric signal in the embodiment described above can be considered as follows. The following explanation will be provided with reference to FIG. 3.

FIG. 3(a) shows an example of the substrate and the reaction field, used for the nucleic acid detection method of the embodiment. The substrate 1 is as described above. The reaction field 10 is formed from the reaction mixture 4. Here, of the ingredients contained in the reaction mixture 4, redox probes 5 and magnesium ion 6a are illustrated for convenience. When amplification products 7 and pyrophosphoric acid molecules 6b are produced by the amplification reaction (FIG. 3 (b)), magnesium ions 6a bond to pyrophosphoric acid molecules 6b to form magnesium pyrophosphate molecules 6. Further, the redox probes 5 may bond to the amplification products 7 to produce complexes 8. The complexes 8 may bond to the magnesium pyrophosphate molecules 6 by electrostastically. In the reaction mixture 4 having a concentration of magnesium ion 6a of 4 mM or higher, magnesium pyrophosphate molecules 6 precipitate on the electrode. Therefore, the complexes 8 may precipitate on the bottom of the reaction field with the precipitation of the magnesium pyrophosphate molecules 6 (FIG. 3 (c)). As the amplification products 7 and/or magnesium pyrophosphate molecules 6 increase, the amount of the precipitate of the complexes 8 may increases. As the amount of precipitate of the complexes 8 increases, the redox probes 5 which approach or contact the electrode 2 increase. Therefore, the electric signal obtained with the electrode 2 increases. With the above-described mechanism, the electric signals from the redox probes 5 bonded to the amplification products 7 existing in the vicinity of the electrode 2 are directly detectable with the electrode. As a result, the amount of the amplification product 7 existing may be reflected as an increase in electric signal in a simple way.

With use of such a detection principle, according to the nucleic acid detection method of the embodiment, it is possible to achieve the detection precisely regardless of the sequence of the target nucleic acid to be detected. Moreover, according to such a detection method, a plurality of target nucleic acids can be detected with high precision in a simple way.

A further embodiment provides a method of detecting a plurality of kinds of target nucleic acids, namely, the first to n-th target nucleic acids.

The first to n-th target nucleic acids respectively contain the $1_1$-th to $1_n$-th sequences, where n is an integer of 2 or greater.

Figure 4:
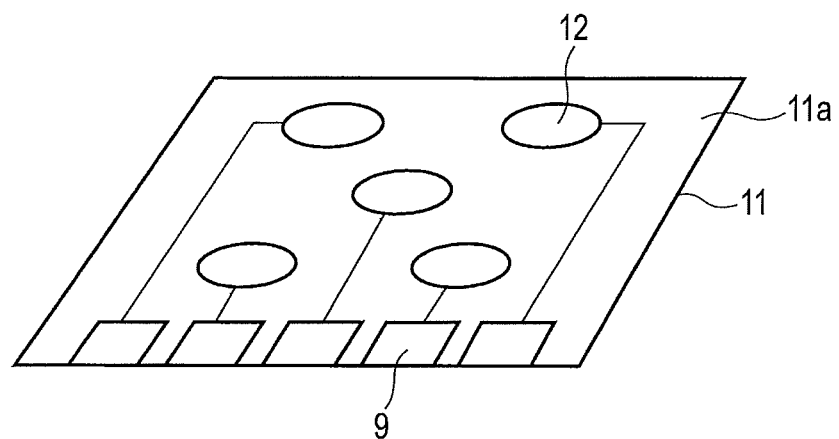
FIG. 4 is a diagram an example of an electrode array for carrying out the method of the embodiment.

In order to detect a plurality of kinds of target nucleic acids such as above, a substrate comprising a plurality of electrodes, i.e., an electrode array, may be used. The substrate shown in FIG. 4 comprises a plurality of electrodes 12 arranged on a surface 11a in contact with a reaction field of the substrate 11, and pads 9 electrically connected to electrodes 12, respectively. The data as electric signals obtained with the electrodes 12 may be extracted from the pads 9.

In order to detect a plurality of kinds of target nucleic acids for one kind of sample, it suffices if, for example, the reaction mixtures each containing primer sets and samples, which correspond to the target nucleic acids to be measured, are spotted respectively to the corresponding electrodes. In this case, the samples should be arranged on the respective electrodes so as not to be brought into contact with each other but only to the respective electrodes. Here, a partition may be provided between electrodes, and further, for example, flow channels independent from each other may be provided to carry the reaction mixtures to the respective electrodes. The example provided above is directed to the case where a plurality of kinds of target nucleic acids are detected for one kind of sample, but it is also possible to similarly detect one kind of target nucleic acid or a plurality of kinds of target nucleic acids by an electrode array for a plurality of kinds of samples. When detecting a plurality of kinds of target nucleic acids, a plurality of kinds of primer sets are used. The plurality of kinds of primer sets may contain primers for amplifying the $1_1$-th to $1_n$-th sequences, respectively.

Moreover, a plurality of kinds of primer sets may be immobilized in advance to a plurality of primer-immobilized regions arranged on a surface in contact with the respective reaction field in an array to be independent from each other.

When a plurality of kinds of primer sets are immobilized onto or near the corresponding electrodes respectively on the electrode array, a plurality of kinds of target nucleic acids contained in one kind of sample can be simultaneously detected with a plurality of electrodes arranged so as to be in contact with the reaction mixture which forms the reaction field.

Figure 5:
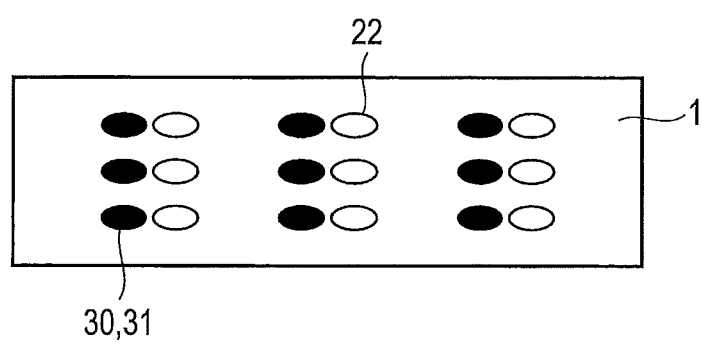
FIG. 5 is a diagram an example of an electrode array for carrying out the method of the embodiment.

The positions of primer-immobilized regions such as above are shown in FIG. 5. For example, as shown in FIG. 5, the electrode array comprises a plurality of electrodes 22 so as to be in contact with one reaction field. In the vicinity of and/or on each of the electrodes 22, a primer-immobilized region 30 is formed and a plurality of primer sets 31 corresponding to the primer-immobilized regions 30 are immobilized by each type. For example, when the positions of the electrodes and the primer sets are tied with each other, it becomes possible to obtain the data of the plurality of kinds of target nucleic acids and the detection results while being associated respectively with each other.

The expression "arranged to be independent from each other" means that the amplification reactions carried out in the reaction fields by specific ones of the plurality of kinds of primer sets are located to be able to achieve the followings: the reactions are not influenced by those carried out by other kinds of primer sets; amplification products produced by the specific primer sets are not mixed with those produced by other kinds of primer sets; and the detection results of the specific amplification products to be detected by the corresponding electrodes can be identified with respect to those of the other amplification products. In order to achieve these, the intervals between the electrodes arranged on the electrode array can be adjusted.

For example, the interval between the electrodes may be 0.1 μm to 10 mm, and the interval between a corresponding electrode and an immobilized region of a respective primer set may be 0.1 μm to 10 mm.

With such structure, it is possible to simultaneously detect a plurality of kinds of target nucleic acids existing in one reaction field.

According to the embodiment described above, it becomes possible to detect a plurality of kinds of sequences efficiently with high sensitivity regardless of the kind of sequence. Moreover, by using the reaction mixture of the composition according to the embodiment, more kinds of sequences can be amplified, for example, efficiently. Therefore, it is possible to detect more kinds of target nucleic acids efficiently with high precision, thereby improving the efficiency of examination.

According to the embodiment described above, there is provided a nucleic acid detection method which can simply detect nucleic acids with high sensitivity.

According to the further embodiment, there is provided an assay kit to detect a target nucleic acid in a sample. The target nucleic acid is as described above, and contains the first sequence. The assay kit contains the composition ingredients of the reaction mixture which forms a reaction field for an amplification reaction to take place.

The composition ingredients of the reaction mixture include a primer set, a specific quantity of magnesium ion, and a redox probe.

The primer set contains at least a first primer complementary to a terminal of the first sequence and a second primer homologous to the other terminal of the first sequence. Such a primer set may be, for example, the above-described primer set.

The magnesium ion may be contained in the assay kit in a specific quantity by which the final concentration thereof in the reaction mixture becomes 4 mM to 30 mM. The magnesium ion may be contained in the kit as magnesium sulfide or magnesium chloride, for example.

The redox probe has an oxidation reduction potential of −0.5 V to 0.5 V and generates a detectable electric signal. The amplitude of the electric signal increases with the increase in the amount of the amplification product existing in a reaction field. The redox probe may be, for example, the one described above.

The assay kit may further contain a reaction reagent. The reaction reagent may be a reagent required for the amplification reaction. The reaction reagent may contain, for example, the above-mentioned corresponding amplification enzyme, a substrate such as deoxynucleoside triphosphate required when forming a new polynucleotide chain with starting from the primer as the starting point, or when reverse transcription to be carried out simultaneously, an enzyme such as reverse transcriptase and a substrate required therefor, and further a buffer for maintaining suitable amplification environment, such as a salt. Further, a thickener may be contained as a reaction reagent.

Each of these composition ingredients of the reaction mixture may be individually contained in the assay kit, or some or all of them may be mixedly contained in the assay kit.

With use of the assay kit containing these ingredients, and for example, the adoption of the above-described nucleic acid detection method, nucleic acids can be detected simply with high sensitivity.

In the further embodiment, the assay kit contains a substrate.

The substrate is for supporting a reaction field for the amplification reaction to take place, formed by the existence of the above-described reaction mixture. The substrate comprises, on a surface thereof, an electrode for detecting an electric signal from a redox probe. The electrode is disposed so as to form the reaction field on itself. Such a substrate may be, for example, the one shown in FIG. 2.

When a substrate is contained in an assay kit, the composition ingredients of the reaction mixture may be releasably immobilized to the surface to be brought into contact with a reaction field of the substrate so as to be brought into the reaction field.

For example, a reaction field may be formed from a reaction mixture containing the composition ingredients, existing on an electrode of the substrate. With use of the reaction field, it is possible to detect nucleic acid simply with high sensitivity.

According to the embodiment described above, there is provided an assay kit which can detect nucleic acid simply with high sensitivity.

EXAMPLES

Example 1

The behavior of the electric signal from RuHex in a LAMP amplification reaction was evaluated.

Preparation of Substrate

Thin films of titanium (500 nm) and gold (2000 nm) were formed on a surface of a Pyrex (registered trademark) glass plate (d=0.8 mm) by sputtering. Then, using a resist AZP4620, a gold electrode (φ=200 μm) was formed. After that, top of it was coated with mercaptohexanol.

LAMP Amplification Reaction

A reaction mixture was prepared, which contains an artificial sequence of parvo virus ($10^5$ copies, 1 μL) (listed in Table 1 as SEQ ID NO: 1) as an amplification product, an F3 primer (SEQ ID NO: 2), a B3 primer (SEQ ID NO: 3), an FIP primer (SEQ ID NO: 4), a BIP primer (SEQ ID NO: 5), an Lb primer (SEQ ID NO: 6) as a LAMP primer shown in Table 2, RuHex (25 microM) as a redox probe, KCl (60 mM), magnesium ion (8 mM), ammonium ion (10 mM), betaine (0.8 M), dNTPs (1.4 mM each) and polymerase (GspSSD) (8 units).

TABLE 1

VP gene of Parvo virus (SEQ ID NO: 1)

AAACGCTAATACGACTCACTATAGGGCGATCTACGGGTACTTTCAATAAT

CAGACGGAATTTAAATTTTTGGAAAACGGATGGGTGGAAATCACAGCAAA

CTCAAGCAGACTTGTACATTTAAATATGCCAGAAAGTGAAAATTATAGAA

GAGTGGTTGTAAATAATTTGGATAAAACTGCAGTTAACGGAAACATGGCT

TTAGATGATACTCATGCACAAATTGTAACACCTTGGTCATTGGTTGATGC

AAATGCTTGGGGAGTTTGGTTTAATCCAGGAGATTGGCAACTAATTGTTA

ATACTATGAGTGAGTTGCATTTAGTTAGTTTTGAACAAGAAATTTTTAAT

GTTGTTTTAAAGACTGTTTCAGAATCTGCTACTCAGCCACCAACTAAAGT

TTATAATAATGATTTAACTGCATCATTGATGGTTGCATTAGATAGTAATA

ATACTATGCCATTTACTCCAGCAGCTATGAGATCTGAGACATTGGGTTTT

TATCCATGGAAACCAACCATACCAACTCCATGGAGATATTATTTTCAATG

GGATAGAACATTAATACCATCTCATACTGGAACTAGTGGCACACCAACAA

ATATATACCATGGTACAGATCCAGATGATGTTCAATTTTATACTATTGAA

AATTCTGTGCCAGTACACTTACTAAGAACAGGTGATGAATTTGCTACAGG

AACATTTTTTTTGATTGTAAACCATGTAGACTAACACATACATGGCAAA

CAAATAGAGCATTGGGCTTACCACCATTTCTAAATTCTTTGCCTCAAGCT

GAAGGAGGTACTAACTTTGGTTATATAGGAGTTCAACAAGATAAAAGACG

TGGTGTAACTCAAATGGGAAATACAAACTATATTACTGAAGCTACTATTA

TGAGACCAGCTGAGGTTGGTTATAGTGCACCATATTATTCTTTTGAGGCG

TCTACACAAGGGCCATTTAAAACACCCTTCCCTTTAGTGAGGGTTAATAA

TABLE 2

| SEQ ID No. | | Sequence |
|---|---|---|
| 2 | F3 | GAGATATTATTTTCAATGGGATAGAAC |
| 3 | B3 | CAATGCTCTATTTGTTTGCCATG |
| 4 | FIP | GAACATCATCTGGATCTGTACCAACCATCTCATACTGGAACTAGTGGC |
| 5 | BIP | CTGTGCCAGTACACTTACTAAGAGTGTTAGTCTACATGGTTTACAATC |
| 6 | Lb | ACAGGTGATGAATTTGCTACAGG |

As a negative control, a sample was further prepared in which the artificial sequence of parvo virus was not added to the reaction mixture. The reaction mixture was brought onto the surface of the substrate having the electrode, and they were warmed isothermally at 67° C., to start the amplification reaction. As the amplification reaction proceeded, the electric signal was measured by a square wave voltammetry (SWV) method.

The results are shown in FIG. 6. FIG. 6(a) is a graph showing the chronological variation in the reduction peak current in each of the case where there was zero copy of artificial sequence (SEQ ID NO: 1) of parvo virus and the case of $10^5$ copies. In the case of $10^5$ copies, the reduction peak current remarkably increased. FIG. 6(b) is a graph showing the chronological variation in the reduction peak potential in each of the case where there was zero copy of artificial sequence of parvo virus and the case of $10^5$ copies. In the case of $10^5$ copies, the reduction peak potential shifted. These results suggest that when an amplification product exists in the reaction mixture containing RuHex, the reduction peak current and the reduction peak potential increase.

Example 2

The behavior of the electric signal from RuHex in the LAMP amplification was evaluated for reaction mixtures containing including different numbers of copies of the amplification product.

Five reaction mixtures similar to that of Example 1 were prepared, which respectively contain zero copy, $10^2$ copies, $10^3$ copies, $10^4$ copies and $10^5$ copies of the artificial sequence (SEQ ID NO: 1) of parvo virus. With use of substrates similar to that of Example 1, these reaction mixtures were warmed isothermally at 67° C., to start the amplification reactions. As the amplification reactions proceeded, the electric signals were measured by the SWV method.

Figure 7:
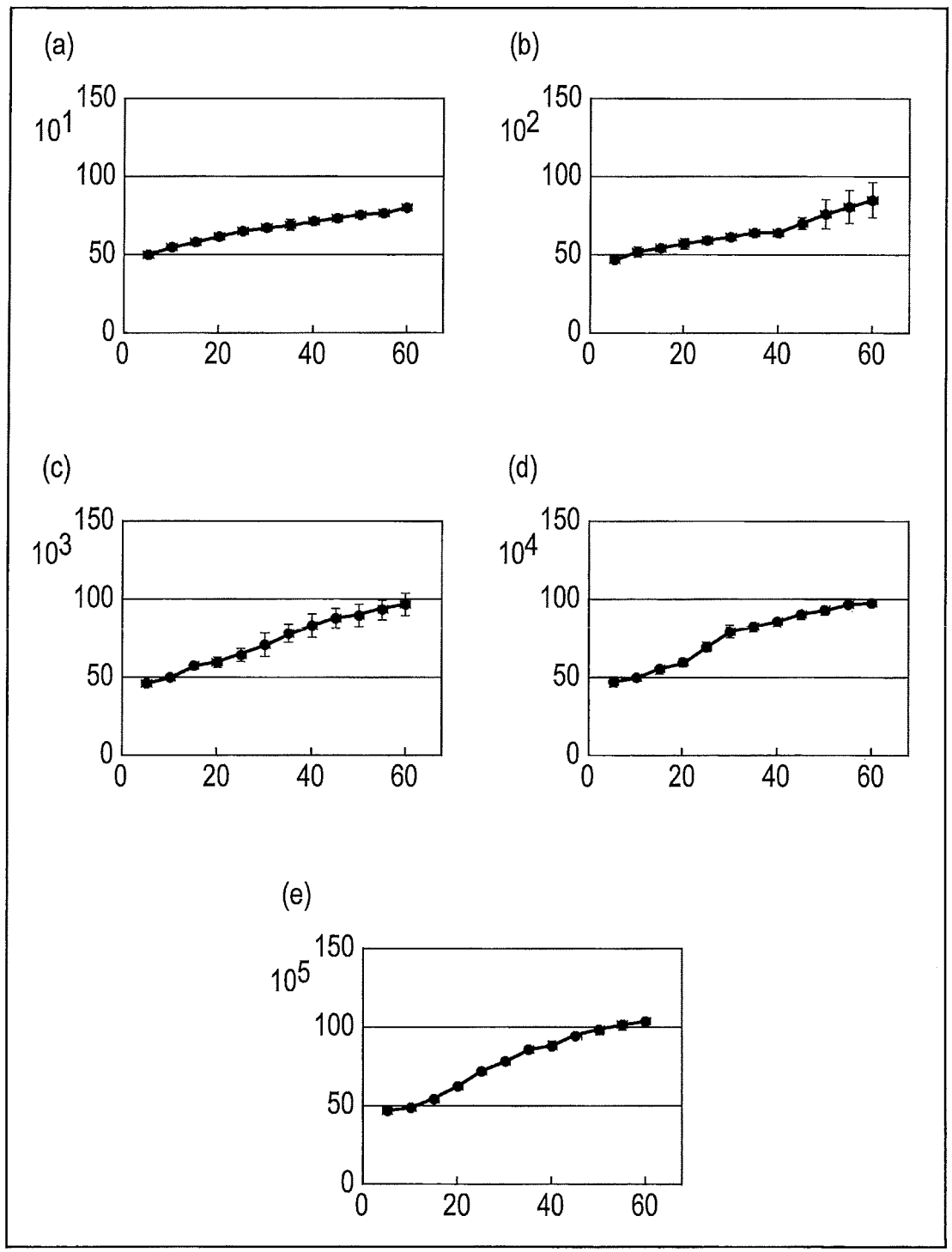
FIG. 7 is a diagram showing the experimental results in Example 2.
Figure 8:
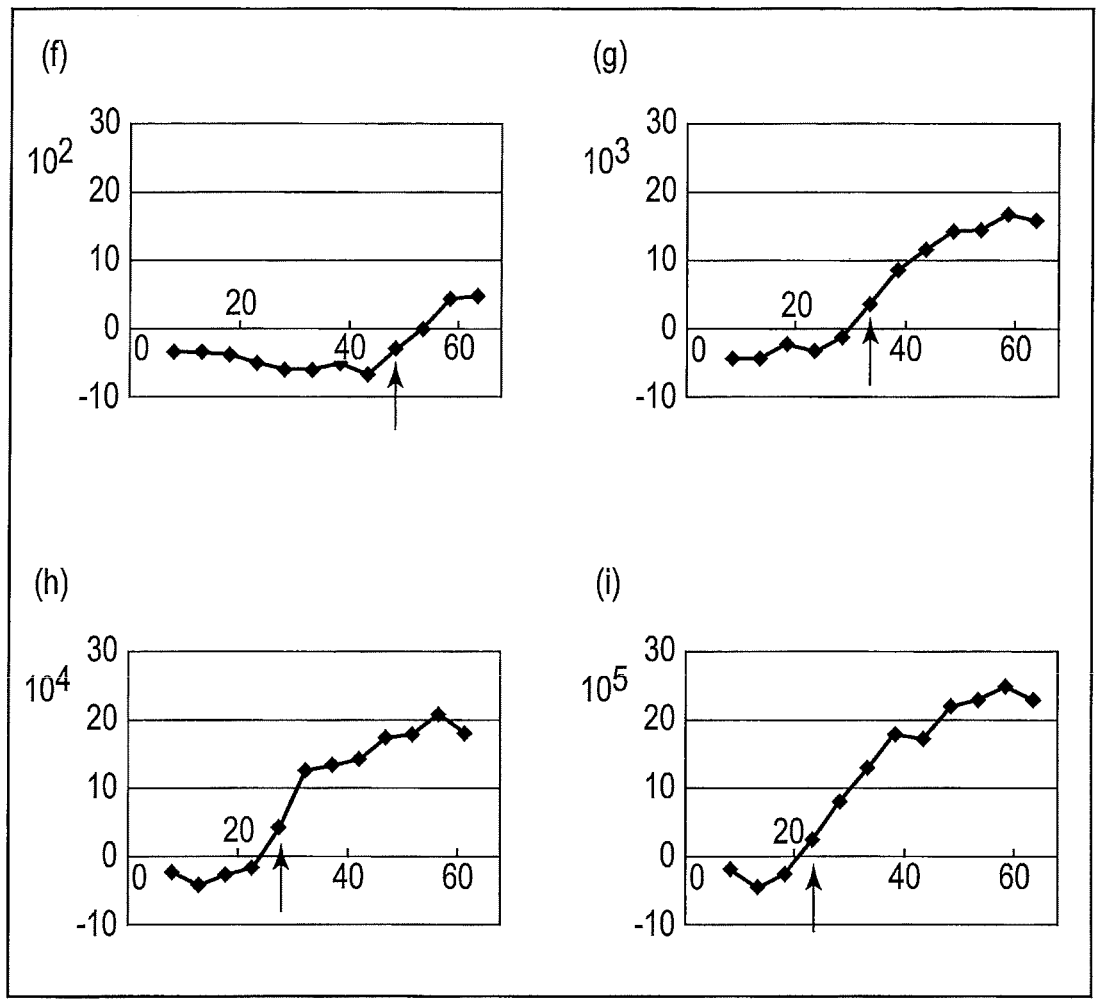
FIG. 8 is a diagram showing the experimental results in Example 2.
Figure 9:
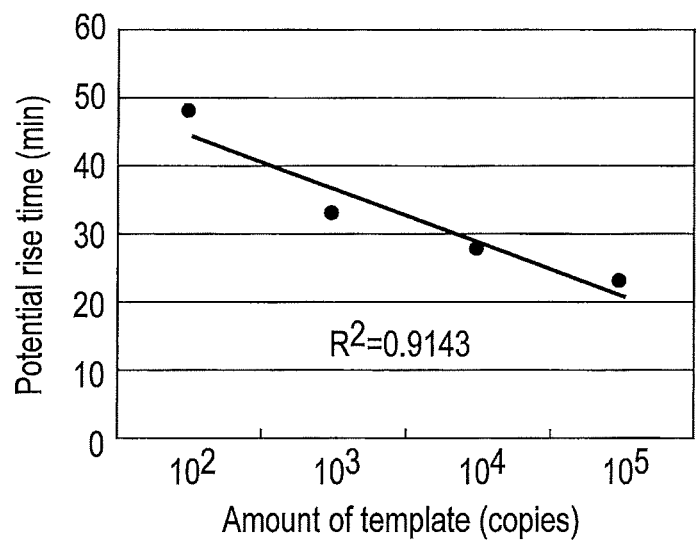
FIG. 9 is a diagram showing the experimental results in Example 2.

The results were shown in FIGS. 7 and 8. FIGS. 7(a) to 7(e) are each a graph showing the chronological variation in the reduction peak potential in the reaction mixture containing the respective number of copies of the artificial sequence of parvo virus. FIGS. 8(f) to 8(i) are each a graphs showing the difference in amount of chronological variation in terms of the reduction peak potential between FIG. 7(a) and each of FIGS. 7(b) to 7(e). In each graph, an arrow indicates the time (potential rise time) when the variation amount of the peak reduction potential shifted by 1 mV/min or more. As the number of copies of parvo virus artificial sequence was greater, the potential rise time was shorter. FIG. 9 is a graph which plotted the potential rise time in each case of the respective numbers of copies of parvo virus artificial sequence, together with a calibration curve. The $R^2$ value of the calibration curve was 0.9143. From these results, it was demonstrated that there is a correlation between the quantity of parvo virus artificial sequence existing and the potential rise time, thus suggesting that the quantity of amplification product in early stages of an amplification reaction can be determined (quantification) based on the potential rise time.

Example 3

The relationship between the quantity of the redox probe, the current and the potential rise time was investigated.

Figure 10:
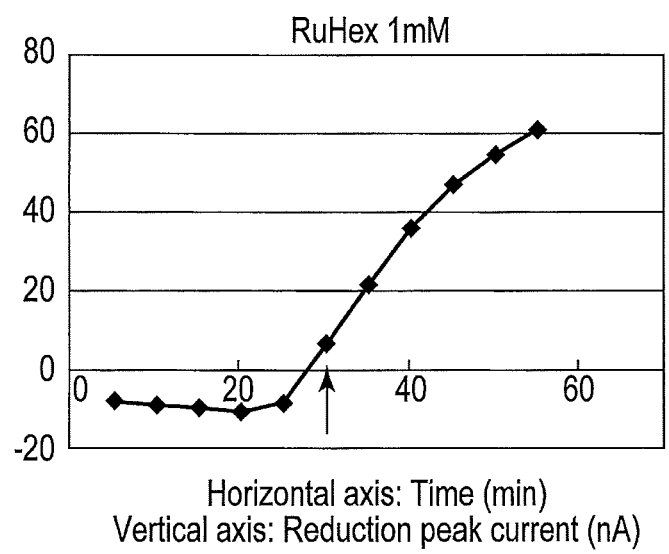
FIG. 10 is a diagram showing the experimental results in Example 3.

A reaction mixture having the same conditions as those of Example 1 except that it contained 1 mM of RuHex and another reaction mixture having the same conditions as that of Example 1 were prepared. With use of a substrate similar to that of Example 1 in the case of $10^5$ copies, each of the reaction mixtures was warmed isothermally at 67° C., to start the amplification reaction. As the amplification reactions proceeded, the electric signals were measured by a linear sweep voltammetry (LSV) method (sweep rate: 0.1 V/s). The results are shown in FIG. 10. The variation amount of the reduction peak current was greater than that of the condition where RuHex was 25 µM (FIG. 6(a)). Thus, it was suggested that when the concentration of the redox probe in the reaction mixture was 1 mM, the detection sensitivity was improved as compared to the case of 25 µM. If the concentration of RuHex was 3 mM or more, the amplification reaction was inhibited; therefore a preferable range is 25 µM to 3 mM.

Example 4

The chronological variations of the current and potential rise time of reaction mixtures containing different numbers of copies of amplification product were investigated using an array electrode.

Production of Chip

Thin films of titanium (500 nm) and gold (2000 nm) were formed on a surface of a Pyrex (registered trademark) glass plate (d=0.8 mm) by sputtering. Then, using a resist AZP4620, sixty gold electrodes (active electrodes) (φ=200 µm) arranged in an array were formed. For every two active electrodes, a reference electrode and a counter electrode were formed to corresponding thereto. After that, top of it was coated with mercaptohexanol.

LAMP Reaction

Five reaction mixtures similar to that of Example 1 were prepared, which respectively contain zero copy, $10^2$ copies, $10^3$ copies, $10^4$ copies and $10^5$ copies of the artificial sequence (SEQ ID NO: 1) of parvo virus. These reaction mixtures were brought onto the surface of the substrate having electrodes, and they were warmed isothermally at 67° C., to start the amplification reactions. As the amplification reactions proceeded, the electric signals were measured by the LSV method (sweep rate: 0.5 V/s).

The results are shown in FIG. 11. FIG. 11(a) is a graph showing the chronological variation in current value. As the number of copies of the artificial sequence of parvo virus was greater, the current rise time was shorter. FIG. 11(b) is a graph which plotted the current rise time in each case of the respective numbers of copies of parvo virus artificial sequence, together with a calibration curve. The $R^2$ value of the calibration curve was 0.9071. From these results, it was demonstrated that there is a correlation between the quantity of parvo virus artificial sequence existing and the current rise time. Thus, it was suggested that with use of a substrate comprising electrodes arranged in an array, the quantity of amplification product in early stages of an amplification reaction can be determined (quantification) based on the potential rise time.

Example 5

The chronological variations in peak current value of reaction mixtures containing different concentrations of magnesium were investigated. The reaction mixtures were prepared from the same ingredients as those of Example 1 except that they respectively contain 2.0 mM, 3.5 mM, 4 mM and 4.5 mM of magnesium ion, and $10^3$ copies of the parvo virus artificial sequence (SEQ ID NO: 1) and RuHex (1 mM). Each of the reaction mixtures was brought onto the surface of a substrate such as of Example 1 having the electrode without application of mercaptohexanol, and was warmed isothermally at 65° C., to start the amplification reaction. As the amplification reactions proceeded, the electric signals were measured by the LSV method (sweep rate: 0.5 V/s).

Figure 12:
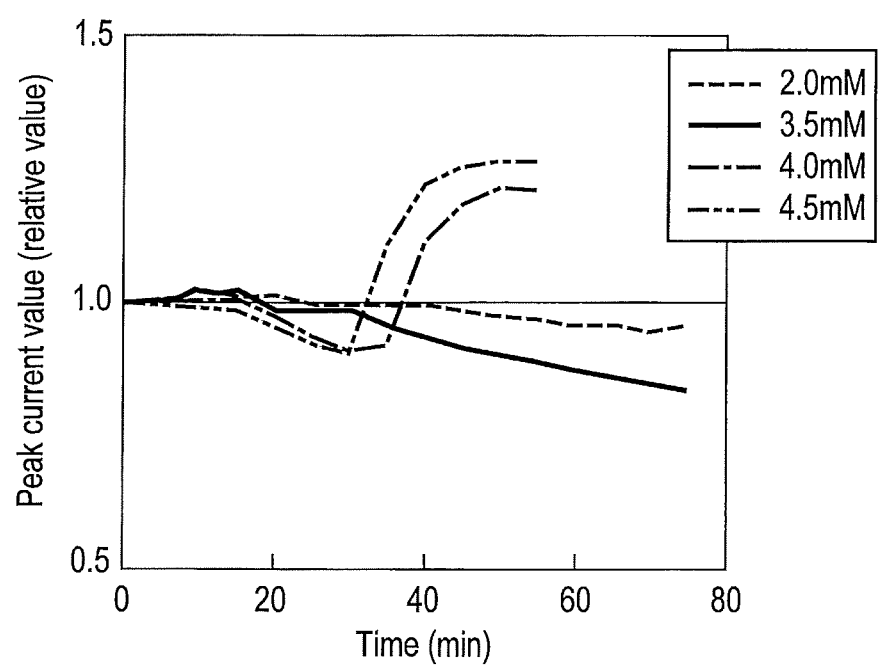
FIG. 12 is a diagram showing the experimental results in Example 5.

The results are shown in FIG. 12. FIG. 12 is a graph showing the chronological variation in relative value of the peak current value with respect to the peak current value before the starting of the amplification reaction start being set to a value of 1. In the reaction mixture having a magnesium ion concentration of 3.5 mM or lower, the current value decreased as the amplification reaction advanced. In the reaction mixture having a magnesium ion concentration of 4 mM or higher, the current value decreased once, and then increased. In the case where the magnesium ion concentration was 4.5 mM, the current rise time was shorter than the case of 4 mM, and the obtained current value itself was high.

Based on these results, it was suggested that when magnesium ion concentration was 4 or more mM, the amplified nucleic acid can be detected based on the increase in current value. Further, as the magnesium ion concentration was higher, the current value was higher. Therefore, it was estimated that RuHex bonded to the precipitate of magnesium pyrophosphate and condensed, and thus the RuHex concentration on the surface of the electrode increased, thereby raising the current value.

Example 6

The LAMP amplification reactions in reaction mixtures containing different concentrations of magnesium ion were investigated.

The reaction mixtures were prepared from the same ingredients as those of Example 1 except that they respectively contain 2.0 mM to 12 mM of magnesium ion, and $10^3$ copies of the parvo virus artificial sequence (SEQ ID NO: 1). 20 µL of each of the reaction mixtures was dispensed into a respective 0.2-mL tube, and warmed isothermally at 65° C., to start the amplification reaction. After 60 minutes of the amplification reaction in each mixture, the existence of the amplification product was examined by electrophoresis.

The results are shown in Table 3. In the reaction mixture having a magnesium ion concentration of 4 mM or more, a typical rudder-shaped band was confirmed in the LAMP reaction.

Based on these results, it was demonstrated that when the magnesium ion concentration was 4 mM or higher, the amplification product was produced by the LAMP reaction.

TABLE 3

| $MgSO_4$ (mM) | Amplification (Presence of band in electrophoresis) |
| --- | --- |
| 2 | x |
| 4 | o |
| 6 | o |
| 8 | o |
| 10 | o |
| 12 | o |

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A method for detecting target nucleic acid in a sample, the target nucleic acid including a first sequence, the method comprising:
   (A) forming a reaction field by placing a reaction mixture on an electrode,
   the reaction mixture comprising:
   the sample;
   a primer set for amplifying the first sequence to obtain an amplification product, wherein the primer set contains at least a first primer complementary to a terminal of the first sequence and a second primer homologous to the other terminal of the first sequence;
   a corresponding amplification enzyme;
   4 mM to 30 mM in concentration of magnesium ion; and
   a redox probe having an oxidation reduction potential of −0.5 V to 0.5 V, which generates a detectable electric signal;
   (B) maintaining the reaction field under an amplification reaction condition to generate the amplification product, wherein, with the increase in the amount of the amplification product, a magnesium pyrophosphate is generated from the magnesium ion and the magnesium pyrophosphate precipitates with the redox probe on the electrode;
   (C) chronologically detecting the electric signal from the redox probe with the electrode while maintaining the reaction field under the amplification reaction condition, wherein the electric signal increases with the increase in the amount of the amplification product present in a reaction field; and
   (D) determining existence or quantity of the target nucleic acid based on chronological variation in the amplitude of the electric signal, obtained in (C).

2. The method of claim 1, wherein
the redox probe is a complex which contains, as a central metal, ruthenium, rhodium, platinum, cobalt, chromium, cadmium, nickel, zinc, copper, osmium, iron, or silver, or a pigment selected from methylene blue, Nile blue and crystal violet.

3. The method of claim 2, wherein
the complex is selected from the group consisting of an amine complex, a cyano complex, a halogen complex, a hydroxy complex, a cyclopentadienyl complex, a phenanthroline complex and a bipyridine complex.

4. The method of claim 1, wherein
the redox probe is ruthenium hexaamine.

5. The method of claim 1, wherein
a concentration of the redox probe is 25 µM or higher and 3 mM or less.

6. The method of claim 1, wherein
the electric signal is an oxidation reduction potential.

7. The method of claim 1, wherein
the electric signal is an oxidation reduction current.

8. The method of claim 1, wherein
the amplification reaction condition is an isothermal amplification reaction condition.

9. The method of claim 8, wherein
the isothermal amplification reaction condition is a LAMP amplification reaction condition.

10. The method of claim 1, wherein
the corresponding amplification enzyme is Bst, GspSSD, or Tin polymerase.

11. The method of claim 1, wherein
the electrode is formed of gold.

12. The method of claim 1, wherein
the redox probe is ruthenium hexaamine, and
no nucleic acid probe is immobilized on the reaction field.

* * * * *

SEQUENCE LISTING

<160> NUMBER OF SEQ ID NOS: 6

<210> SEQ ID NO 1
<211> LENGTH: 1000
<212> TYPE: DNA
<213> ORGANISM: Parvo virus

<400> SEQUENCE: 1

```
aaacgctaat acgactcact atagggcgat ctacgggtac tttcaataat cagacggaat      60
ttaaattttt ggaaaacgga tgggtggaaa tcacagcaaa ctcaagcaga cttgtacatt     120
taaatatgcc agaaagtgaa aattatagaa gagtggttgt aaataatttg gataaaactg     180
cagttaacgg aaacatggct ttagatgata ctcatgcaca aattgtaaca ccttggtcat     240
tggttgatgc aaatgcttgg ggagtttggt ttaatccagg agattggcaa ctaattgtta     300
atactatgag tgagttgcat ttagttagtt ttgaacaaga aatttttaat gttgttttaa     360
agactgtttc agaatctgct actcagccac caactaaagt ttataataat gatttaactg     420
catcattgat ggttgcatta gatagtaata atactatgcc atttactcca gcagctatga     480
gatctgagac attgggtttt tatccatgga aaccaaccat accaactcca tggagatatt     540
attttcaatg ggatagaaca ttaataccat ctcatactgg aactagtggc acaccaacaa     600
atatatacca tggtacagat ccagatgatg ttcaatttta tactattgaa aattctgtgc     660
cagtacactt actaagaaca ggtgatgaat ttgctacagg aacatttttt tttgattgta     720
aaccatgtag actaacacat acatggcaaa caaatagagc attgggctta ccaccatttc     780
taaattcttt gcctcaagct gaaggaggta ctaactttgg ttatatagga gttcaacaag     840
ataaaagacg tggtgtaact caaatgggaa atacaaacta tattactgaa gctactatta     900
tgagaccagc tgaggttggt tatagtgcac catattattc ttttgaggcg tctacacaag     960
ggccatttaa aacacccttc cctttagtga gggttaataa                          1000
```

<210> SEQ ID NO 2
<211> LENGTH: 27
<212> TYPE: DNA
<213> ORGANISM: Artificial Sequence
<220> FEATURE:
<223> OTHER INFORMATION: Synthetic primer

<400> SEQUENCE: 2

```
gagatattat tttcaatggg atagaac                                          27
```

<210> SEQ ID NO 3
<211> LENGTH: 23
<212> TYPE: DNA
<213> ORGANISM: Artificial Sequence
<220> FEATURE:
<223> OTHER INFORMATION: Synthetic primer

<400> SEQUENCE: 3

```
caatgctcta tttgtttgcc atg                                              23
```

<210> SEQ ID NO 4
<211> LENGTH: 48
<212> TYPE: DNA
<213> ORGANISM: Artificial Sequence
<220> FEATURE:

-continued

```
<223> OTHER INFORMATION: Synthetic primer

<400> SEQUENCE: 4
gaacatcatc tggatctgta ccaaccatct catactggaa ctagtggc                    48

<210> SEQ ID NO 5
<211> LENGTH: 48
<212> TYPE: DNA
<213> ORGANISM: Artificial Sequence
<220> FEATURE:
<223> OTHER INFORMATION: Synthetic primer

<400> SEQUENCE: 5
ctgtgccagt acacttacta agagtgttag tctacatggt ttacaatc                    48

<210> SEQ ID NO 6
<211> LENGTH: 23
<212> TYPE: DNA
<213> ORGANISM: Artificial Sequence
<220> FEATURE:
<223> OTHER INFORMATION: Synthetic primer

<400> SEQUENCE: 6
acaggtgatg aatttgctac agg                                               23
```